(12) United States Patent
Shimada

(10) Patent No.: US 8,562,919 B2
(45) Date of Patent: Oct. 22, 2013

(54) FECES SAMPLING CONTAINER

(75) Inventor: Yasumasa Shimada, Chuo-ku (JP)

(73) Assignee: Kyowa Medex Co., Ltd., Tokyo (JP)

( * ) Notice: Subject to any disclaimer, the term of this patent is extended or adjusted under 35 U.S.C. 154(b) by 3 days.

(21) Appl. No.: 13/133,519

(22) PCT Filed: Dec. 1, 2009

(86) PCT No.: PCT/JP2009/006513
§ 371 (c)(1),
(2), (4) Date: Jun. 8, 2011

(87) PCT Pub. No.: WO2010/067534
PCT Pub. Date: Jun. 17, 2010

(65) Prior Publication Data
US 2011/0243816 A1 Oct. 6, 2011

(30) Foreign Application Priority Data
Dec. 12, 2008 (JP) .................................. 2008-316626

(51) Int. Cl.
B01L 3/00 (2006.01)
B01L 3/14 (2006.01)
G01N 1/04 (2006.01)
G01N 1/12 (2006.01)

(52) U.S. Cl.
USPC ........ 422/547; 422/549; 422/550; 73/864.41; 73/864.51; 73/864.91

(58) Field of Classification Search
None
See application file for complete search history.

(56) References Cited

U.S. PATENT DOCUMENTS

| 5,246,669 A | 9/1993 | Hayashi |  |
| 5,514,341 A | * 5/1996 | Urata et al. | ................... 422/534 |

(Continued)

FOREIGN PATENT DOCUMENTS

| CN | 1053741 C | 6/2000 |
| CN | 1985166 A | 6/2007 |

(Continued)

OTHER PUBLICATIONS

International Search Report for PCT/JP2009/006513, dated Mar. 2, 2010.

(Continued)

Primary Examiner — Jill Warden
Assistant Examiner — Charles D Hammond
(74) Attorney, Agent, or Firm — Westerman, Hattori, Daniels & Adrian, LLP

(57) ABSTRACT

It is to provide a device for sampling feces that enables an accurate and quantitative evaluation by decreasing the variations of feces sampling levels, wherein the confirmation of the presence or absence of feces sampling can be performed hygienically and simply from an outside of a container. A device for sampling feces comprising a feces sampling stick 10, a container body 20, and a fitting body (30, 40) fitted to the inner part of the container body; the feces sampling stick having a gripping part 11 and a stick part 12, being provided with a feces sampling part 14 at the end; the container body having an opening part to fit the fitting body on one side, and a bottom part 21 on the other side, wherein a feces-suspending liquid container part for preserving a liquid for suspending feces 22 is formed in a space between the lower part of the container body and the lower side of the fitting body; the fitting body having a tubular guide part 34 that enables introduction of the stick part of the feces sampling stick, a first leveling hole 35 to remove excess feces, and a second leveling hole 42 below the first hole for further removing excess feces; wherein a domain for detecting collected feces 39 is formed in a tubular guide part adjacent to the upper end of the first leveling hole.

12 Claims, 11 Drawing Sheets

(56) References Cited

U.S. PATENT DOCUMENTS

| | | |
|---|---|---|
| 7,908,935 B2 | 3/2011 | Hasegawa et al. |
| 2008/0034899 A1* | 2/2008 | Kikuiri ............... 73/864.51 |
| 2009/0053111 A1* | 2/2009 | Francis .................. 422/102 |
| 2010/0000341 A1 | 1/2010 | Hasegawa et al. |

FOREIGN PATENT DOCUMENTS

| | | |
|---|---|---|
| JP | 64-42454 U | 3/1989 |
| JP | 4-59468 U | 5/1992 |
| JP | 5-071749 U | 9/1993 |
| JP | 6-74965 A | 3/1994 |
| JP | 6-148178 A | 5/1994 |
| JP | 6-74965 U | 10/1994 |
| JP | 7-049345 A | 2/1995 |
| JP | 8-166765 A | 6/1996 |
| JP | 9-015239 A | 1/1997 |
| JP | 10-319844 A | 12/1998 |
| JP | 2005-249553 A | 9/2005 |
| JP | 2007-170997 A | 7/2007 |
| WO | 2007/069731 A1 | 6/2007 |

OTHER PUBLICATIONS

Notification of Transmittal of Translation of the International Preliminary Report on Patentability (Form PCT/IB/338) of International Application No. PCT/JP2009/006513 mailed Jul. 14, 2011with Forms PCT/IB/373 and PCT/ISA/237.

Chinese Office Action dated Dec. 31, 2012, issued in corresponding Chinese patent application No. 200980149362.4.

* cited by examiner

A-A' CROSS-SECTION

2mg

C-C' CROSS-SECTION 0.8mg

FECES SAMPLING CONTAINER

TECHNICAL FIELD

The present invention relates to a feces sampling container, more specifically, a feces sampling container capable of reducing variations in the sampling amount of feces and enabling hygienic and easy confirmation, from the outside of the container, of whether or not the feces have been collected.

BACKGROUND ART

Feces expelled from animals including humans are very useful for an occult blood test, i.e., for the diagnosis of various diseases such as tumors of lower gastrointestinal tracts including large intestine and therefore are used widely as a clinical test sample. For the above diagnosis, a constant amount of feces should be collected and then buffered with a proper liquid. In order to achieve this requirement by using a simple, hygienic, and accurate means and realize hygienic storage and transport of collected feces, various feces sampling containers have been developed and reported (see, for example, patent documents 1 to 8).

However, the above feces sampling containers have sometimes difficulty in adjusting the sampling amount of feces upon quantitative test, depending on the characteristic and appearance of feces to be tested because feces differ in characteristic and appearance, and in addition to normal feces, there are, for example, high fiber feces and watery feces. Further, due to a difference in the characteristic and appearance, etc. of the feces to be tested, the sampling amount varies greatly among feces samples.

In various clinical tests using feces samples, particularly a test for an antigen contained in the feces samples by utilizing an antigen-antibody reaction, a predetermined sampling amount is required to be secured irrespective of the characteristic and appearance of the feces to be tested. At the same time, the concentration of feces in a feces sample buffer should be a constant level, but it is difficult to carry out a quantitative test by using the above feces sampling containers.

Moreover, there has not been a full investigation of a feces sampling container permitting hygienic and easy confirmation, from the outside of the container, of whether or not the feces have been collected upon carrying out the test.

PRIOR ART DOCUMENTS

Patent Documents

Patent Document 1: Japanese Unexamined Utility Model Application Publication No. 5-71749
Patent Document 2: Japanese Unexamined Patent Application Publication No. 7-49345
Patent Document 3: Japanese Unexamined Utility Model Application Publication No. 1-42454
Patent Document 4: Japanese Unexamined Patent Application Publication No. 2005-249553
Patent Document 5: Japanese Unexamined Patent Application Publication No. 9-15239
Patent Document 6: Japanese Unexamined Utility Model Application Publication No. 4-59468
Patent Document 7: Japanese Unexamined Patent Application Publication No. 6-148178
Patent Document 8: Japanese Unexamined Utility Model Application Publication No. 6-74965

SUMMARY OF THE INVENTION

Object to be Solved by the Invention

An object of the present invention is to provide a feces sampling container capable of reducing variations in the sampling amount of feces and thereby realizing an accurate quantitative evaluation, and in addition, permitting hygienic and easy confirmation, from the outside of the container, of whether or not the feces have been collected.

Means to Solve the Object

The present inventors have carried out an intensive investigation with a view to satisfying the above object. As a result, it has been found that the above object can be satisfied by providing a feces sampling container equipped with a feces sampling stick, a container body, and a fitting body fitted to the inner part of the container body, wherein the feces sampling container has a fitting body structure in which the fitting body is equipped with a first leveling hole provided in the vicinity of the tip of the stick part of the feces sampling stick for removing excess feces attached to a feces sampling part and a second leveling hole provided below the first leveling hole for further removing excess feces to ensure constant sampling of feces; and has a feces sampling-stick structure in which the stick part has, at the base end thereof, a screw part for inserting the feces sampling stick in the fitting body while screwing the stick in order to transfer the excess feces removed using the first leveling hole to a collected-feces detecting domain; wherein the collected-feces detecting domain is formed by a helical structure protruded into the inner side surface of a tubular guide part of the fitting body, and thus completed the present invention.

The present invention relates to [1] a feces sampling container equipped with a feces sampling stick, a container body, and a fitting body to be fitted to the inner part of the container body, wherein the feces sampling stick has a gripping part on one side thereof, a stick part on the other side, and a feces sampling part in the vicinity of the tip of the stick part; the container body has an opening part for fitting the fitting body therein on one side, a bottom part on the other side, and a feces-suspending liquid container part for preserving a liquid for suspending feces therein in a space between the lower part of the container body and the lower side of the fitting body; the fitting body has a tubular guide part that enables introduction of the stick part of the feces sampling stick, a first leveling hole provided in the tubular guide part for removing excess feces, and a second leveling hole provided below the first leveling hole for removing excess feces further; and a collected-feces detecting domain is formed in the tubular guide part adjacent to the upper end of the first leveling hole.

The present invention also relates to [2] the feces sampling container according to [1] wherein the feces sampling stick is equipped, at the base end of the stick part thereof, with a screw part for screwing and inserting the feces sampling stick in the fitting body; [3] the feces sampling container according to [1] or [2], wherein the feces-suspending liquid container part preserves therein the liquid for suspending feces and the feces sampling part in the vicinity of the tip of the stick part of the feces sampling stick penetrates through the first leveling hole and the second leveling hole of the fitting body and is dipped in the liquid for suspending feces; [4] the feces sampling container according to any one of [1] to [3] wherein the feces sampling part in the vicinity of the stick part of the feces sampling stick is equipped with a concave part, a through-hole, or a trench part; [5] the feces sampling container according to any one of [1] to [4], wherein the bottom part of the container body is a recessed bottom equipped with a pierce part, [6] the feces sampling container according to any one of [1] to [5], wherein an opening area of the second leveling hole of the fitting body is smaller than an opening area of the first leveling hole; [7] the feces sampling container according to any one of [1] to [6], wherein the opening area of the first leveling hole of the fitting body is smaller than the cross-sectional area of the feces sampling part of the feces sampling stick; [8] the feces sampling container according to any one of [2] to [7], wherein the collected-feces detecting domain is formed by a helical structure protruding to the inner surface side of the tubular guide part of the fitting body; and [9] the feces sampling container according to [8], wherein the helical structure is formed so that a helix rotation angle of the feces sampling stick to be screwed and inserted is set at within from 200 to 260 degrees.

The present invention further relates to [10] the feces sampling container according to [1] to [9], wherein the fitting body is comprised of an upper fitting block and a lower fitting block and the upper fitting block has the first leveling hole of the tubular guide part; [11] the feces sampling container according to [10], wherein the lower fitting block has the second leveling hole and a support part for supporting the lower side part of the tubular guide part in the upper fitting block; [12] the feces sampling container according to [1] to [11], wherein the fitting body further has, below the second leveling hole thereof, a filter part; and [13] the feces sampling container according to any one of [1] to [12], wherein a label is stuck in a J shape to the outside of the feces sampling container over a part from the gripping part to one of the side surfaces, the bottom, and the other side surface of the container body and the label is provided with a cutout window for confirming collection of feces, from which the collected-feces detecting domain can be seen directly.

Effect of the Invention

When the feces sampling container according to the present invention is used, a sufficient sampling amount of feces is ensured and variations in sampling amount of feces are reduced irrespective of the characteristic and appearance of the feces to be tested so that this makes it possible to realize an accurate quantitative evaluation and improve the accuracy of a clinical test using feces samples thus collected. Moreover, the feces sampling container according to the present invention enables hygienic and easy confirmation of whether or not the feces have been collected from the outside of the container.

MODE OF CARRYING OUT THE INVENTION

Figure 1:
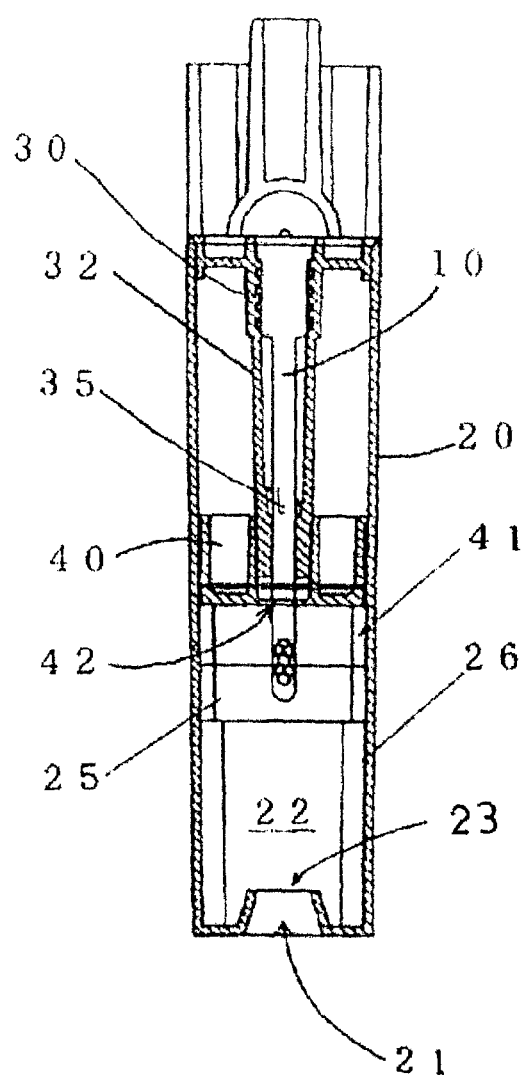
FIG. 1 is a see-through front view of the feces sampling container according to the present invention.

As the feces sampling container of the present invention, any feces sampling container is usable insofar as it is a feces sampling container equipped with a feces sampling stick, a container body, and a fitting body to be fitted to the inner part of the container body, wherein the feces sampling stick has a gripping part on one side thereof and a stick part on the other side and at the same time, it has a feces sampling part in the vicinity of the tip of the stick part; the container body has, on one side thereof, an opening part for fitting the fitting body therein and a bottom part on the other side; a feces-suspending liquid container part for preserving a liquid for suspending feces therein is formed in a space between the lower part of the container body and the lower side of the fitting body; the fitting body has a tubular guide part allowing insertion of the stick part of the feces sampling stick therein, a first leveling hole provided in the tubular guide part for removing excess feces, and a second leveling hole provided below the first leveling hole for removing excess feces further; and a collected-feces detecting domain is formed at the tubular guide part adjacent to the upper end of the first leveling hole. The feces sampling container of the present invention usually has a configuration in which the fitting body is fitted in the container body, a liquid for suspending feces is preserved in a feces-suspending liquid container part formed between the lower side of the container body and the lower side of the fitting body, and the feces sampling stick is inserted through the first leveling hole and the second leveling hole provided in the fitting body in order of mention from the opening part side to the bottom part of the container body. The present invention is however not limited to this configuration, and for example the feces sampling stick can be attached to the side surface of the container body.

The gripping part provided on one side of the feces sampling stick has preferably a shape functioning as a cap member of the feces sampling container for preventing leakage and scattering of, before a feces sampling operation, the liquid for suspending feces and, after the feces sampling operation, a fecal suspension obtained by suspending feces in the liquid for suspending feces. For example, a gripping part having a lower end with a flange shape or skirt-like shape is preferred. It may be subjected to appropriate surface treatment to facilitate holding of it upon sampling of feces. In order to impart the liquid-tight function to the feces sampling stick equipped with the gripping part as a cap member, it is also possible to provide a screw part at the base end of the stick part of the feces sampling stick and install the feces sampling stick under a liquid tight condition by screwing and inserting the feces sampling stick in the fitting body or to construct so that the base end portion of the stick part of the feces sampling stick can be inserted in the inner peripheral surface of the opening part of the container body under close contact. As described later, it is more preferred to provide the base end of the stick part of the feces sampling stick with a screw part. The structure of the feces sampling part in the vicinity of the tip of the stick part of the feces sampling stick may be determined from the standpoint of a balance between ease of manufacture and sampling of a constant amount. Examples of the structure include one or more structures selected from various shapes of concave part, through-hole, trench part (annular trench, elongated trench, helical trench, diagonal-line trench, V-shaped trench) and the like. With regards to the length of the stick part of the feces sampling stick, the feces sampling part in the vicinity of the tip of the stick part is long enough to pass through the second leveling hole provided in the fitting body. When the feces-suspending liquid container part is filled with the liquid for suspending feces, the feces sampling part in the vicinity of the tip of the stick part of the feces sampling stick is preferably long enough to penetrate through the first leveling hole and the second leveling hole of the fitting body and be dipped in the liquid for suspending feces. The feces sampling stick is made of, for example, low-density polyethylene, ABS resin, or the like.

As to the container body, there is no restriction as long as it is a bottomed tubular container with a rectangular, oblong or rounded cross-section having, on one side thereof, an opening part for fitting therein the fitting body and a bottom part on the other side. The container body having a concave bottom equipped with a pierce part, particularly, a tapered concave bottom which is tapered toward the bottom part is preferred in order to steadily introduce the tip of a suction nozzle for a fecal suspension to the pierce part and steadily carry out sampling. The concave bottom part with the pierce part preferably has strength or structure permitting perforation by the tip of the suction nozzle for the fecal suspension. It is also preferred to preserve a liquid for suspending feces in the feces-suspending liquid container part formed between the lower side of the container body and the lower part of the fitting body in advance. In a preferred embodiment in which a filter part is provided below the second leveling hole of the fitting body, a filter member can be integrated in a bowl shape with the fitting body at the lower portion thereof, and the filter member is preferably placed at a position below the fitting body as a separate member from the fitting body. When the filter member and the fitting body are separated, the filter member can be fixed by fitting it in the container body or by using a filter member support separately.

As to the material of the container body, there is no restriction as long as it is a plastic material which enables looking in from the outside. Preferred examples of it include flexible resins such as polypropylene, polyethylene, polyester, and polyvinyl chloride. As the filter member, any material is usable insofar as it can filter undigested solid matters which will interfere with a test and does not adsorb a substance to be detected. In general, materials available at a low cost, for example, filter paper, sponge, absorbent cotton, and sintered bodies of a synthetic resin such as polypropylene or polyethylene can be used preferably.

As to the liquid for suspending feces, there is no restriction as long as it is a solution capable of suspending therein feces collected by the feces sampling part of the feces sampling stick. Examples include aqueous mediums such as deionized water, distilled water, and buffer. Of these, the buffer is preferred. Examples of the buffer include a phosphate buffer, a carbonate buffer, an ammonia buffer, an acetate buffer, a lactate buffer, a citrate buffer, a tartrate buffer, a borate buffer, a glycine buffer, and a Good's buffer. Examples of buffers used as a Good's buffer include 2-amino-2-hydroxymethyl-1,3-propanediol, 2-morpholinoethanesulfonic acid, piperazine-bis(2-ethanesulfonic acid), (2-acetamido)-2-aminoethanesulfonic acid, bis(2-hydroxyethyl)-2-aminoethanesulfonic acid, bis(2-hydroxyethyl)iminotris (hydroxymethyl)methane, 3-[bis(2-hydroxyethyl)amino]-2-hydroxypropanesulfonic acid, 2-hydroxyethylpiperazine-3-propanesulfonic acid, hydroxyethylpiperazine-2-ethanesulfonic acid, 2-hydroxyethylpiperazine-2-hydroxypropane-3-sulfonic acid, 3-(morpholino) propanesulfonic acid, 3-(morpholino)-2-hydroxypropanesulfonic acid, piperazine-bis(2-hydroxypropanesulfonic acid), tris(hydroxymethyl)methyl-2-hydroxy-3-aminopropanesulfonic acid, tris (hydroxymethyl)methyl-2-aminomethanesulfonic acid, 2-acetamidoiminodiacetic acid, bis(2-hydroxyethyl)glycine, tris(hydroxymethyl)methylglycine, and bis(2-hydroxyethyl) iminotris(hydroxymethyl)methane.

The liquid for suspending feces can further contain an antiseptic, an antibiotic, an organic acid, a sugar, a protein, a ferrocyanic compound, a chelating agent, a salt, a protease inhibitor, or the like.

Examples of the antiseptic include thimerosal, dichlorohexidyl, and azides. The azides include lithium azide, sodium azide, potassium azide, ammonium azide, and the like.

Examples of the antibiotic include β-lactam antibiotics, tetracycline antibiotics, macrolide antibiotics, aminoglycoside antibiotics, nucleoside antibiotics, ansamycin antibiotics, polypeptide antibiotics, and other antibiotics.

Examples of the β-lactam antibiotics include penicillins, cephalosporins, thienamycin, and sulfazecin. The penicillins include penicillin G, penicillin N, penicillin O, penicillin V, and the like. The cephalosporins include cephamycin A, cephamycin B, cephamycin C, cephalosporin, cephalothin, cephalonium, cephalexin, cephradine, hetasporin, cefapirin, loracarbef, and the like.

Examples of the tetracycline antibiotics include minocycline, tetracycline, hydroxytetracyclin, chronocycline, terramycin, nitrocycline, amicycline, anthracycline, metacycline, deoxycycline, glycocycline, and anhydrotetracycline.

Examples of the macrolide antibiotics include acetylspiramycin, erythromycin, picromycin, pimaricin, lucensomycin, amphotericin B, candicidin A, and candicidin B.

Examples of the aminoglycoside antibiotics include streptomycin, streptomycin B, dehydrostreptomycin, oxystreptomycin, kanamycin, kasugamycin, gentamycin A, gentamycin C, lincomycin, bleomycin, and mannoside hydroxystreptomycin.

Examples of the nucleoside antibiotics include polyoxin A, polyoxin B, polyoxin C, polyoxin D, polyoxin E, polyoxin F, polyoxin G, polyoxin H, polyoxin J, polyoxin K, polyoxin L, polyoxin M, tubercidin, and formycin B.

Examples of the ansamycin antibiotics include ansamycin, rifamycin, rifamycin B, rifamycin L, rifamycin S, rifamycin V, rifamycin Y, and rifampicin.

Examples of the polypeptide antibiotics include polymyxin, gramycin A, gramycin B, gramycin C, viomycin, bacitracin, actinomycin, tyrocidine A, tyrocidine B, tyrocidine C, tyrocidine D, tyrocidine S, and staphylomycin.

Examples of other antibiotics include cycloheximide, cycloserin, sarcomycin A, spectinomycin, chloramphenicol, mitomycin, blasticidin S, fumagillin, monensin, pyrrolnitrin, and phosphonomycin.

The above antibiotics can form salts. Examples of the salts include acid addition salts (hydrochlorides, sulfates, phosphates, acetates, fumarates, oxalates, tartrates, etc), ammonium salts, organic amine added salts (triethylamine salts, etc.), and metal salts (lithium salts, sodium salts, potassium salts, magnesium salts, calcium salts, etc.).

Examples of the organic acid include malic acid or salts thereof, succinic acid or salts thereof, fumaric acid or salts thereof, glycolic acid or salts thereof, 2-ketoglutaric acid or salts thereof, isocitric acid or salts thereof, lactic acid or salts thereof, pyruvic acid or salts thereof, uric acid or salts thereof, and oxaloacetic acid or salts thereof. Examples of the salt include ammonium salts, sodium salts, potassium salts, calcium salts, and magnesium salts.

Examples of the sugar include glucose, sucrose, maltose, cyclodextrins, fructose, sorbose, saccharose, lactose, trehalose, galacturonic acid, mannitol, D-glucosamine, mannose, cellobiose, glycidol, and innositol. The cyclodextrins include α-cyclodextrin, β-cyclodextrin, γ-cyclodextrin, hydroxypropyl-α-cyclodextrin, hydroxypropyl-β-cyclodextrin, hydroxypropyl-γ-cyclodextrin, β-cyclodextrin polymer, dimethyl-β-cyclodextrin, 6-O-α-maltosyl-α-cyclodextrin, 6-O-α-maltosyl-β-cyclodextrin, sulfated α-cyclodextrin, and 2,3,6-tri-O-methyl-β-cyclodextrin. As these cyclodextrins, commercially available products (for example, product of Nihon Shokuhin Kako) can also be used.

Examples of the protein include albumins and iron proteins. The albumins include serum albumin, ovalbumin, and lactoalbumin. Of these, serum albumin is preferred. As the serum albumin, that prepared using the plasma of mammals such as humans, cows, and horses in accordance with a routine method or a commercially available one is usable. The serum albumin is preferably bovine serum albumin (which will hereinafter be abbreviated as "BSA") or human serum albumin. An albumin-containing serum is also usable. Examples of the iron proteins include non-heme iron proteins and heme iron proteins. Examples of the non-heme iron proteins include holo-transferrin, apo-transferrin, lactoferrin, ferritin, hemosiderin, ferredoxin, and oxygenase, while examples of the heme-iron proteins include hemoglobin of animals other than humans, ferricytochrome c, myoglobin, peroxidase, and catalase.

Examples of the ferrocyan compounds include sodium ferrocyanide, potassium ferrocyanide, 11-ferrocenyl-1-undecanethiol, 8-ferrocenyl-1-octanethiol, 6-ferrocenyl-1-hexanethiol, 11-ferrocenylundecyl polyoxyethylene ether, and 11-ferrocenyltrimethylundecyl ammonium bromide.

Examples of the chelating agent include ethylenediaminetetraacetic acid or salts thereof, O,O'-bis(2-aminophenyl)ethyleneglycol-N,N,N',N'-tetraacetic acid or salts thereof, trans-1,2-diaminocyclohexane-N,N,N',N'-tetraacetic acid or salts thereof, 1,3-diamino-2-hydroxypropane-N,N,N',N'-tetraacetic acid or salts thereof, diethylenetriamine-N,N,N',N'',N''-pentaacetic acid or salts thereof, ethylenediamine-N,N'-diacetic acid or salts thereof, ethylenediamine-N,N'-bis(methylenephosphonic acid) or salts thereof, N-(2-hydroxyethyl)ethylenediamine-N,N',N'-triacetic acid or salts thereof, ethylenediamine-N,N',N',N'-tetrakis(methylenephosphonic acid) or salts thereof, 0,0'-bis(2-aminoethyl)ethyleneglycol-N,N,N',N'-tetraacetic acid or salts thereof, N,N'-bis(2-hydroxybenzyl)ethylenediamine-N,N'-diacetic acid or salts thereof, 1,6-hexamethylenediamine-N,N,N',N'-tetraacetic acid or salts thereof, N-(2-hydroxyethyl)iminodiacetic acid or salts thereof, iminodiacetic acid or salts thereof, 1,2-diaminopropane-N,N,N',N'-tetraacetic acid or salts thereof, nitrilotriacetic acid or salts thereof, nitrilotripropionic acid or salts thereof, nitrilotris(methylenephosphonic acid) or salts thereof, N,N,N',N'-tetrakis(2-pyridylmethyl) ethylenediamine or salts thereof, and triethylenetetramine-N,N',N'',N''',N''''-hexaacetic acid or salts thereof. Examples of these salts include ammonium salts, sodium salts, potassium salts, magnesium salts, and calcium salts.

Examples of the salts include sodium chloride, sodium sulfate, potassium chloride, potassium sulfate, magnesium chloride, magnesium sulfate, magnesium acetate, lithium chloride, lithium sulfate, ammonium chloride, ammonium sulfate, magnesium nitrate, and calcium nitrate.

Examples of the protease inhibitor include Complete (trade mark, produced by Roche), antipapain dihydrochloride, aprotinin, chymostatin, E-64, leupeptin, Pefabloc (trade mark, produced by Roche), pepstatin, phosphoramidon, antithrombin III, (4-aminodiphenyl)methanesulfonyl fluoride, calpain inhibitor 1,3,4-dichloroisocoumarin, α-macroglobulin, and bestatin.

The feces collected using the feces sampling stick are caused to pass through the first leveling hole and the second leveling hole of the fitting body to remove excess feces and then suspended in the liquid for suspending feces preserved in the feces-suspending liquid container part to give a fecal suspension. The fecal suspension may contain a solid matter and the solid matter in the fecal suspension is removed through the filter part and the fecal suspension from which the solid matter has been removed is filled in a space between the filter of the feces-suspending liquid container part and the concave bottom of the container body. After the solid-matter-free fecal suspension filled in the space is withdrawn using a puncture needle such as injection needle, it can be provided for an analysis system. Alternatively, after the space is filled with the solid-matter-free fecal suspension, the concave bottom of the container body is turned up by turning the container body upside down and then, a puncture needle such as injection needle is pierced into the concave bottom of the container body which is turned upside to withdraw the solid-matter-free fecal suspension without the puncture needle reaching the filter part.

The filter part is provided in a space between the second leveling hole and the concave bottom of the container body. The tip part of the feces sampling stick may not penetrate but stick into the filter part or may be retained between the second leveling hole and the filter part while the feces sampling stick is inserted in the second leveling hole through the tubular guide part. Either mode is possible.

As to the fitting body to be fitted to the inner part of the container body, there is no restriction as long as it has a tubular guide part capable of liquid-tightly shielding the upper inside part of the container body from the feces-suspending liquid container part provided in the lower inside part, and permitting insertion of the stick part of the feces sampling stick, a first leveling hole provided in the tubular guide part for removing excess feces, a second leveling hole provided below the first leveling hole for removing excess feces further, and a collected-feces detecting domain formed at the tubular guide part adjacent to the upper end of the first leveling hole. Example of the fitting body include a fitting body comprised of a single fitting block provided, at the tubular guide part thereof, with the first leveling hole and the second leveling hole; and a fitting body comprised of a plurality of fitting blocks, for example, a fitting block comprised of an upper fitting block provided, at the tubular guide part thereof, the first leveling hole and a lower fitting block provided with the second leveling hole. When the fitting body is comprised of a single fitting block, a fixing member for fixing a portion of the tubular guide part in the vicinity of the lower end thereof to the container body is preferably formed integrally with the tubular guide part. In the case where a fitting body is comprised of an upper fitting block and a lower fitting block and the upper fitting block has a first leveling hole of the tubular guide part, the lower fitting block is preferably provided with a hold part for the lower portion of the tubular guide part in the upper fitting block. The fitting body described above can be fixed liquid-tightly by fitting it in the container body or fixed liquid-tightly by using a fitting body support separately.

For removing excess feces attached to the feces sampling part of the feces sampling stick using the first leveling hole and for sampling a constant amount of feces by removing excess feces further using the second leveling hole, the opening area (hole diameter) of the second leveling hole provided in the fitting body is preferably made smaller than the opening area (hole diameter) of the first leveling hole. In addition, the opening area (hole diameter) of the first leveling hole or the second leveling hole of the fitting body is preferably smaller than the cross-sectional area (stick diameter) of the feces sampling part of the feces sampling stick. By making the opening area (hole diameter) of the first leveling hole of the fitting body smaller than the cross-sectional area (stick diameter) of the feces sampling part of the feces sampling stick, excess feces attached to the feces sampling part of the feces sampling stick can be removed efficiently through the first leveling hole. By making the opening area (hole diameter) of the second leveling hole of the fitting body smaller than the cross-sectional area (stick diameter) of the feces sampling part of the feces sampling stick or the opening area (hole diameter) of the first leveling hole, sampling of a constant amount of feces through the second leveling hole can be achieved. Moreover, in order to prevent leakage of the liquid for suspending feces, the second leveling hole can be provided with a thin membrane sealing film or the second leveling hole can be made as a structure in which the second leveling hole is closed when the stick part of the feces sampling stick is pulled out.

A collected-feces detecting domain can be formed in the tubular guide part adjacent to the upper end of the first leveling hole, for example, by employing a method of accumulating and storing excess feces removed through the first leveling hole in the tubular guide part adjacent to the upper end of the first leveling hole so as to hygienically and easily confirm whether or not the feces have been collected, from the outside of the container. Described specifically, the opening area of the first leveling hole is smaller than the internal cross-sectional area of the tubular guide part adjacent to the upper end of the first leveling hole, to form a shape having a different level, so that the excess feces attached to the feces sampling part of the feces sampling stick are accumulated and stored in this part having a different level. This reduced diameter part functions as the collected-feces detecting domain. When this part having a different level is inclined, excess feces, especially soft excess feces, can be accumulated and stored efficiently in the bottom of this part having a different level.

In the case where the feces sampling stick is equipped, at the base end of the stick part thereof, with a male screw part for screwing the feces sampling stick while inserting the feces sampling stick into a female screw provided at the upper part of the fitting body, excess feces attached to the feces sampling part of the feces sampling stick slide down on the downward helix slope of the helical structure due to a friction pressure when the feces sampling container of the invention is equipped with the above part having a different level, while being compressed by the helical structure protruding to the inner surface side of the tubular guide part adjacent to the upper end of the first leveling hole of the fitting body. The feces are accumulated and stored in the non-different level portion of the protruding helical structure and this non-different level portion of the protruding helical structure placed at a predetermined position in advance is formed as the collected-feces detecting domain. It is particularly preferred to form the helical structure so that the helix rotation angle of the feces sampling stick to be inserted while screwed be set within a range of from 200 to 260 degrees, because excess feces attached to the feces sampling part of the feces sampling stick slide down on the downward helix slope of the helical structure by a friction pressure while being compressed by the helical structure protruding to the inner surface side of the tubular guide part and then are accumulated and stored in the non-different level portion of the protruding helical structure (from 160 to 100 degrees).

The tubular guide part preferably has a gradual reverse tapered structure, which terminates at the part having a different level at the upper end of the first leveling hole. Such a structure enables smooth introduction of the feces sampling part of the feces sampling stick to the first leveling hole. The reverse tapered structure extending from the first leveling hole to the upper part adjacent to the second leveling hole or extending from the first leveling hole to the second leveling hole is preferred because it can smoothly guide the feces sampling part of the feces sampling stick from first leveling hole to the second leveling hole. A portion of the tubular guide part downward from the first leveling hole has usually a tubular shape having the same diameter.

As the material for forming the fitting body, soft flexible resins such as polyethylene, polypropylene, polyester, soft polyvinyl chloride, and olefin elastomer can be commonly used in consideration of the liquid-tight sealing property, attachment to the container body by insertion, and easy insertion of the feces sampling stick into the first leveling hole or second leveling hole.

It is preferred to attach a label to the outside of the feces sampling container so as to extend it in a J shape from the gripping part to one of the side surfaces, the bottom, and the other side surface of the container body. The label can be provided with a cutout window for confirming collection of feces so that the collected-feces detecting domain can be seen directly. This label can be used not only as a label for identifying the name and sex of the subject, feces collection date, and the like but is also useful for protection or contamination prevention of the pierce part at the bottom of the container body.

One embodiment of the use of the feces sampling container of the present invention will next be described. Take out the feces sampling stick from the feces sampling container and collect feces by sticking the feces sampling part of the feces sampling stick into feces or smearing it with the surface portion of the feces. Then, insert the stick part of the feces sampling stick into the erected container body via a tubular guide part of a fitting body, screw the gripping part of the feces sampling stick into the container body, engage a male screw provided at the base end part of the stick part of the feces sampling stick with a female screw provided at the upper part of the fitting body to hermetically seal the container body. At the same time, insert the feces sampling part of the feces sampling stick through the first leveling hole and the second leveling hole and dip it in the liquid for suspending feces. In this condition, the subject can send the feces sampling container to a hospital or inspection institute by mail or another method after confirming collection of the feces in the collected-feces detecting domain. After reconfirmation of the collection of feces in the collected-feces detecting domain of the feces sampling container at the hospital or inspection institute who has received the container, the hospital or inspection institute can make an inspection by successively penetrating the tip of a suction nozzle of a fecal suspension through the label and the pierce part at the bottom of the container body, with the feces sampling container turned upside down, and suctioning and sending the fecal suspension to an analysis apparatus.

An embodiment of the feces sampling container of the present invention will next be described specifically referring to attached drawings. It should however be borne in mind that the technical scope of the present invention is not limited by these examples.

Figure 2:
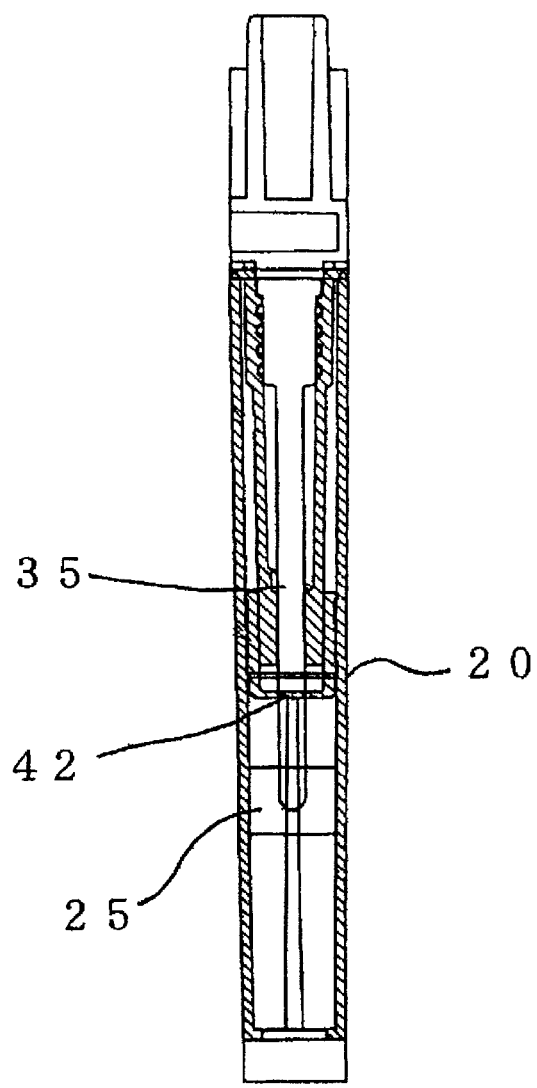
FIG. 2 is a see-through side view of the feces sampling container according to the present invention.
Figure 3:
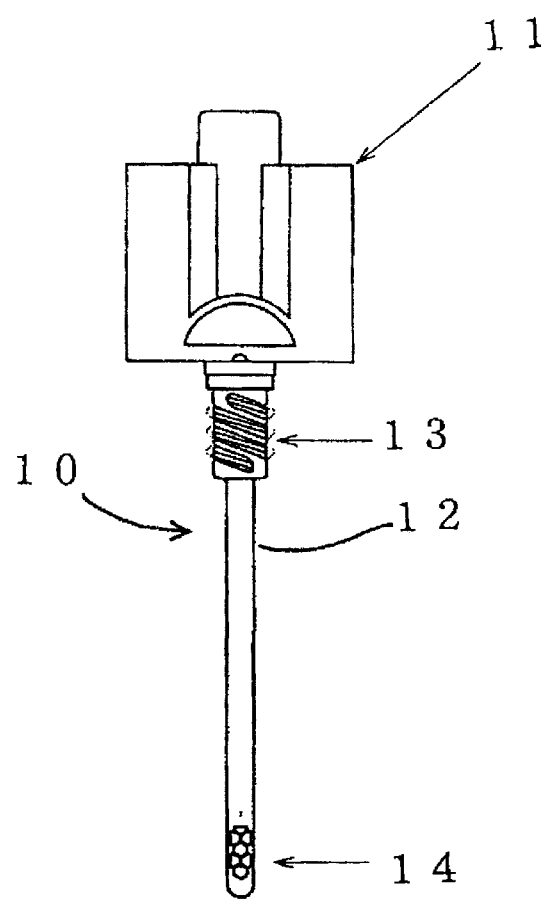
FIG. 3 is a front view of the feces sampling stick of the feces sampling container according to the present invention.
Figure 4:
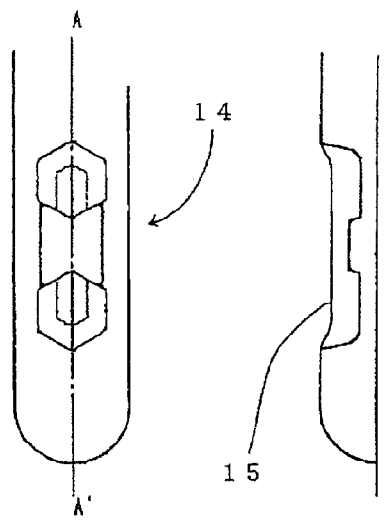
FIG. 4 is an enlarged view of the tip of the feces sampling stick of the feces sampling container according to the present invention.
Figure 4:
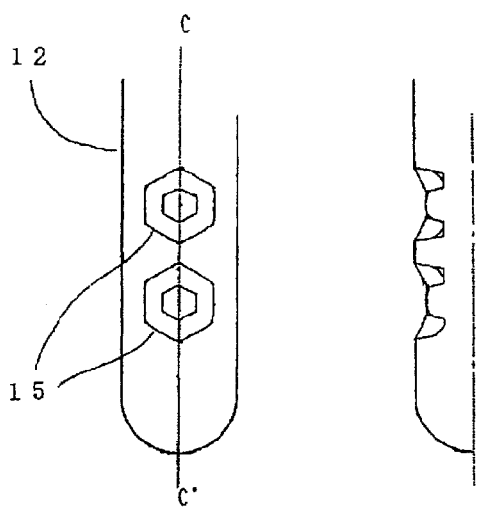
Figure 5:
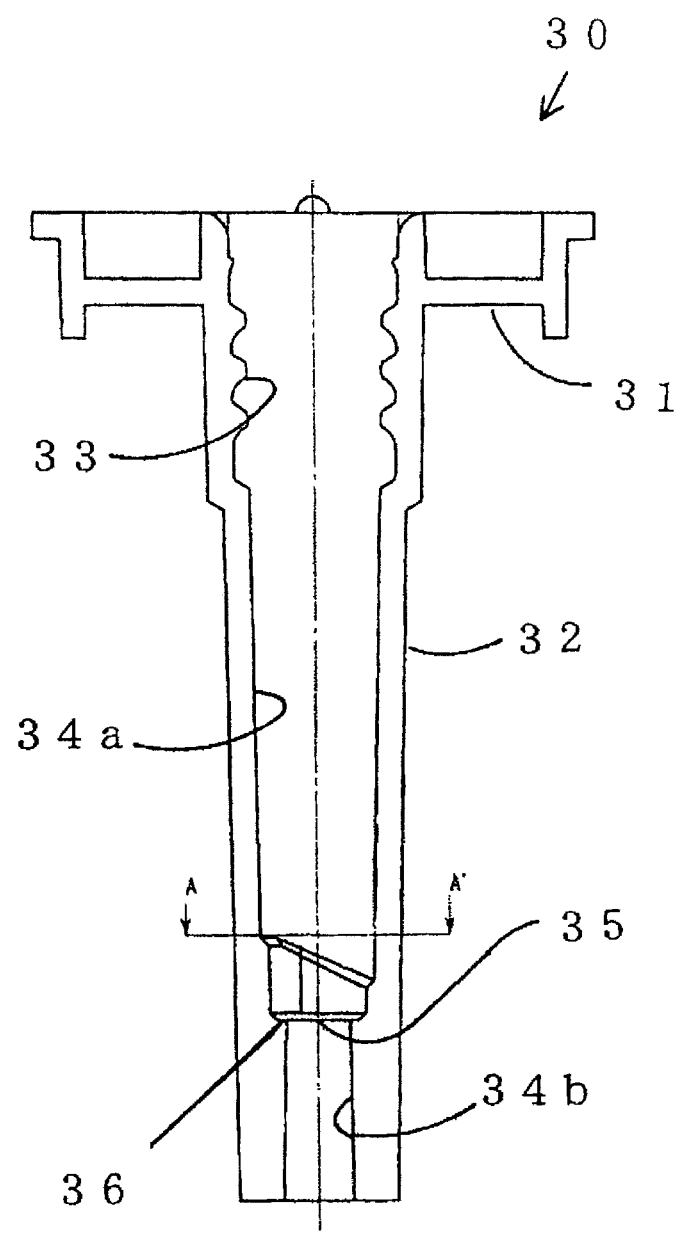
FIG. 5 is a front view of the upper fitting block of the feces sampling container according to the present invention.
Figure 6:
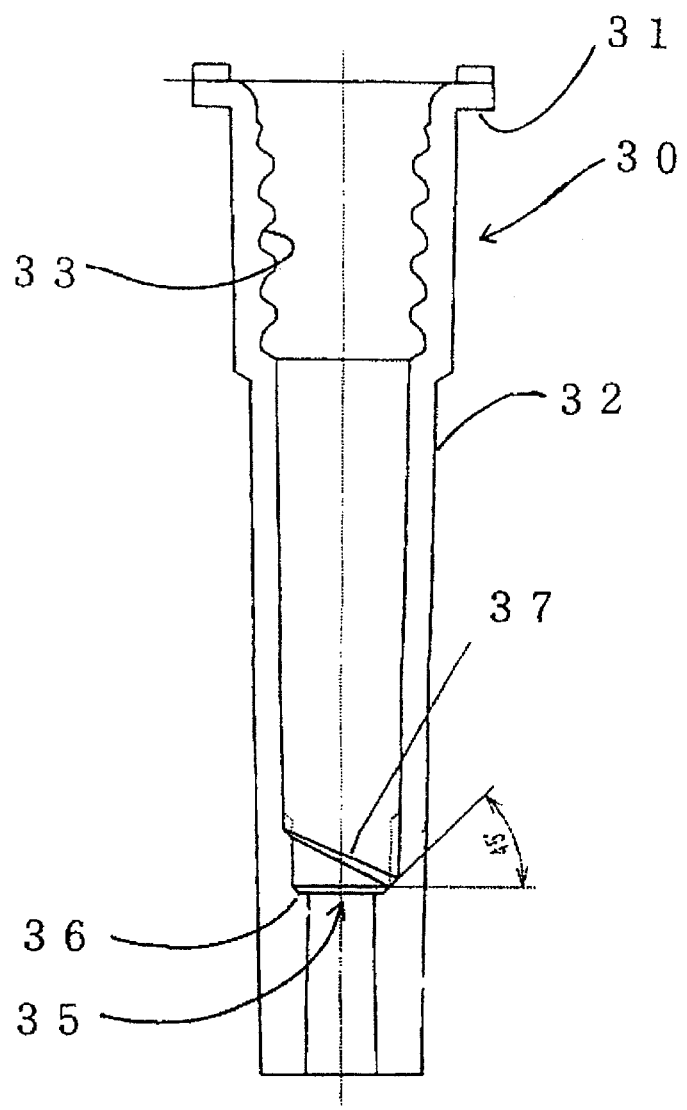
FIG. 6 is a left side view of the upper fitting block of the feces sampling container according to the present invention.
Figure 7:
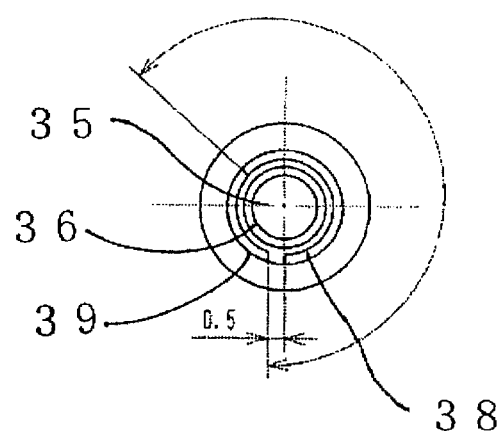
FIG. 7 is a cross-sectional view taken along a line A-A' of FIG. 5.
Figure 8:
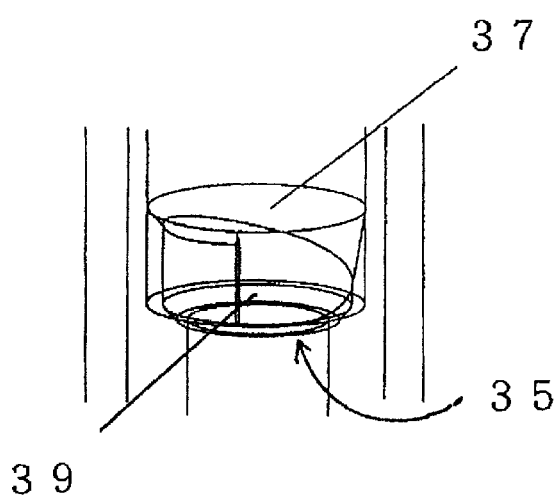
FIG. 8 is a see-through perspective view of the helical structure in the tubular guide part of the upper fitting block of the feces sampling container according to the present invention.
Figure 9:
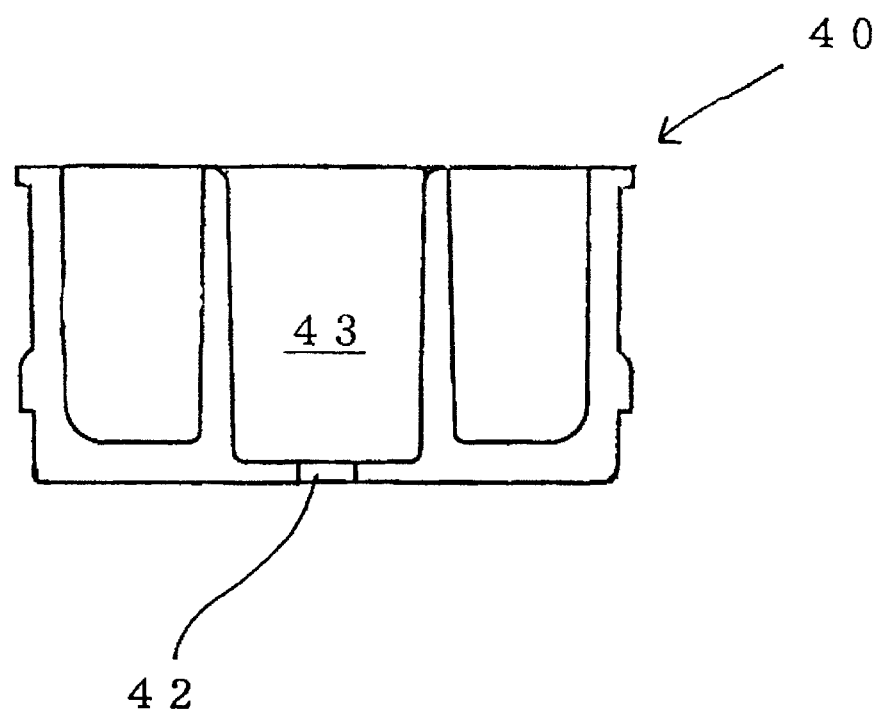
FIG. 9 is a longitudinal cross-sectional view of the lower fitting block of the feces sampling container according to the present invention.
Figure 10:
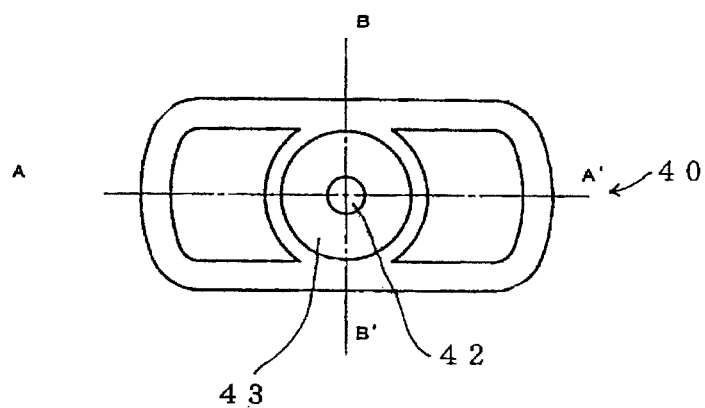
FIG. 10 is a plan view of the lower fitting block of the feces sampling container according to the present invention.
Figure 11:
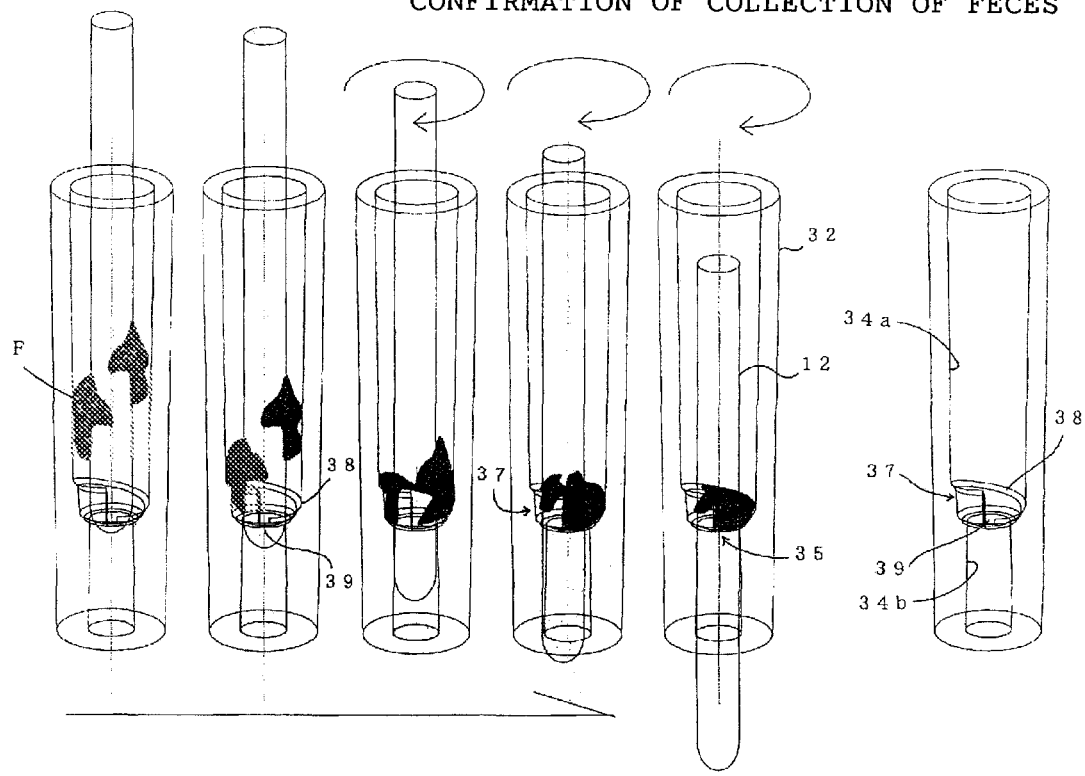
FIG. 11 shows an illustration of the confirmation of collection of feces by using the feces sampling container according to the present invention.
Figure 12:
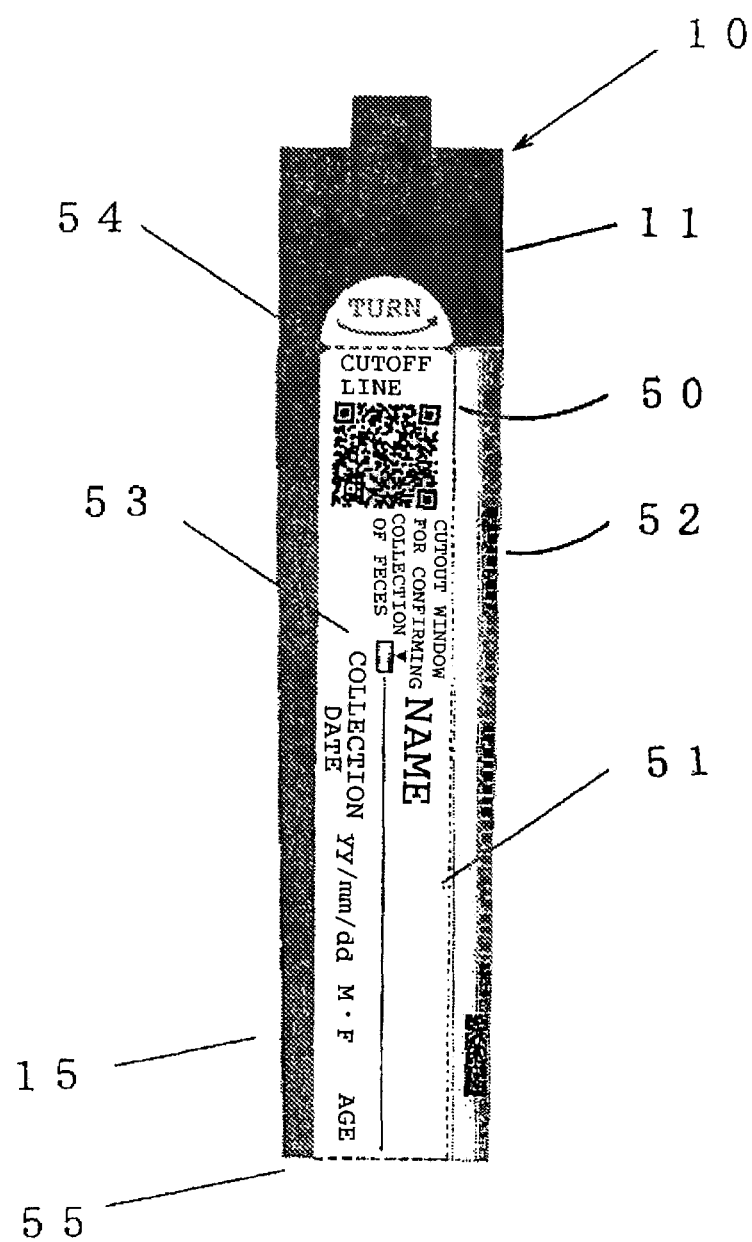
FIG. 12 shows the appearance (front side) of the labeled feces sampling container according to the present invention.
Figure 13:
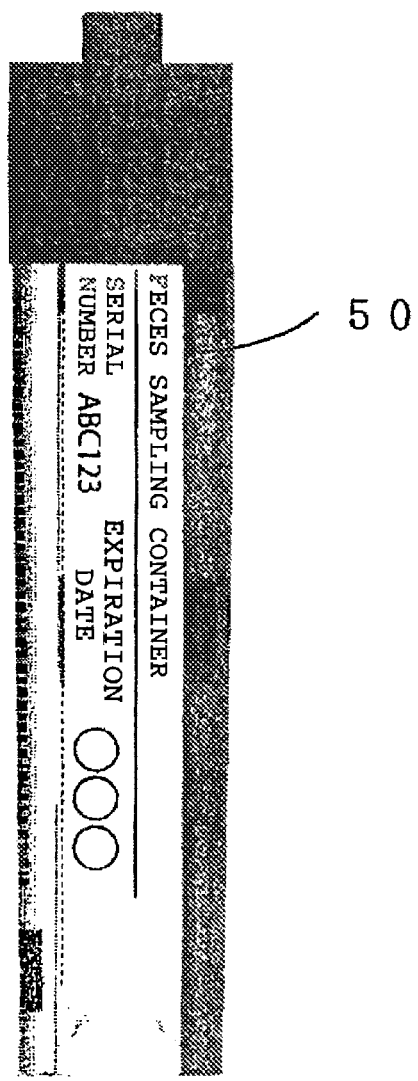
FIG. 13 shows the appearance (back side) of the labeled feces sampling container according to the present invention.

FIG. 1 is a see-through front view of the feces sampling container of the present invention equipped with a feces sampling stick 10, a container body 20, a fitting body comprised of an upper fitting block 30 and a lower fitting block 40 fitted in the inner part of the container body, and a filter 25; FIG. 2 is a see-through side view of FIG. 1; FIG. 3 is a front view of the feces sampling stick 10; FIG. 4 is an enlarged view of the tip of the feces sampling stick; FIG. 5 is a front view of the upper fitting block 30; FIG. 6 is a left side view of the upper fitting block 30; FIG. 7 is a cross-sectional view taken along a line A-A' of FIG. 5; FIG. 8 is a see-through perspective view of a helical structure 37; FIG. 9 is a longitudinal cross-sectional view of the lower fitting block 40; FIG. 10 is a plan view of the lower fitting block 40; FIG. 11 illustrates an image of the confirmation of collection of feces; FIG. 12 illustrates the appearance (front side) of the feces sampling container with a label 50; and FIG. 13 illustrates the appearance (back side) of the feces sampling container with a label 50.

As illustrated in FIGS. 3 and 4, the feces sampling stick 10 has, on one side thereof, a gripping part 11 serving as a cap member of the feces sampling container for preventing leakage and scattering of the sample and, on the other side, a stick part 12 having a diameter of 2.0 mm. The stick part has, at the base end thereof, a male screw part 13 and in the vicinity of the tip, a feces sampling part 14 equipped with a plurality of concave parts 15. FIG. 4 (left side) illustrates a feces sampling part 14 equipped with a concave part 15 for collecting therein 2 mg of feces and FIG. 4 (right side) illustrates a feces sampling part 14 equipped with a concave part 15 for collecting therein 0.8 mg of feces.

As illustrated in FIGS. 1 and 2, the container body 20 is equipped with an opening part for fitting the fitting body and the like therein and is in the shape of a flat rectangular parallelepiped having a bottom and a side peripheral surface. It has, at the bottom thereof, a concave bottom 21 equipped with a pierce part 23. In the container body 20, a filter 25 supported by a filter support 26 is inserted and the lower fitting block 40 is fitted via a lower fitting block support 41. Below the lower fitting block 40, a liquid for suspending feces 22 is preserved. As illustrated in FIGS. 9 to 10, the lower fitting block 40 has a second leveling hole 42 having a hole diameter of 1.4 mm and a hold part 43 consisting of an annular dent for supporting and fixing the lower portion of the upper fitting block.

As illustrated in FIGS. 5 to 8, the upper fitting block 30 is comprised of an upper fitting flange part 31 and a tubular guide member 32 having a gradual reverse tapered shape. The tubular guide member 32 is comprised of a female screw part 33 provided on the upper inner peripheral surface thereof and a tubular guide part 34 followed by the female screw part 33 and permits insertion of the stick part of the feces sampling stick. The tubular guide part 34 is equipped with a first leveling hole 35 having a hole diameter of 1.95 mm for removing excess feces. The tubular guide part 34 adjacent to the upper end of the first leveling hole 35 is constituted as a shape having a different level 36 at which the inner diameter is reduced from 2.9 mm to 2.14 mm. The tubular guide part 34 is formed as an upper tubular guide part 34a that has a decreasing diameter from the upper end to the part having a different level 36; and a lower tubular guide part 34b having the same diameter from the first leveling hole 35 to the lower end. As described above, the lower portion of the tubular guide member 32 is fixed with a hold part 43 consisting of an annular dent of the lower fitting block 40.

The collected-feces detecting domain, which is one of the characteristics of the feces sampling container of the present invention, will next be described. The collected-feces detecting domain is formed at the part having a different level 36 of the tubular guide part 34 adjacent to the upper end of the first leveling hole 35. Through this collected-feces detecting domain, hygienic and easy confirmation of whether or not the feces have been collected, can be carried out from the outside of the container. In the vicinity of the lower end of the upper tubular guide part 34a, a helical structure 37 protruding to the inner surface side of the upper tubular guide part 34a is provided by setting a helix rotation angle of the feces sampling stick 10 to be inserted while being screwed to 229 degrees. As illustrated in FIG. 11, excess feces F attached to the feces sampling part 14 and the like of the feces sampling stick 10 slide down, while being compressed by the helical structure 37 protruding to the inner surface side of the tubular guide part 34a, on a downward helix slope 38 of the helical structure 37. They are accumulated and stored in the non-different level portion 39 (131 degrees) of the protruding helical structure 37. Thus, the non-different level portion 39 of the helical structure 37 is formed as the collected-feces detecting domain.

As illustrated in FIGS. 12 and 13, the label 50 is stuck in the J shape onto the outside of the feces sampling container. It extends from the gripping part 11 of the feces sampling stick 10 through one of the side surfaces (front side), the bottom, and the other side surface (back side) of the container body 30. It is equipped with a data entry column 51 for filling therein data such as the subject's name, sex, age, collection date, and the like and a barcode 52. In addition, the label 50 is stuck so that a cutout window 53 for confirming the collection of feces is located at a position corresponding to the collected-feces detecting domain. This makes it possible to easily confirm whether or not the feces have been collected, from the outside of the container and at the same time, to carry out this confirmation without a discomfort. Further, the label 50 has a perforated line 54 for confirming opening at a position corresponding to a boundary between the gripping part 11 of the feces sampling stick 10 and the container body 30 and the label 50 has a perforated line 55 for test at a position corresponding to a surface side corner on the bottom of the container body. This perforated line 55 for test is used as needed when, with the feces sampling container turned upside down, the label is peeled off from the side surface (back side) and cut off at a position of the label 50 corresponding to the surface-side corner on the bottom of the container body before the tip of the suction nozzle of the fecal suspension is penetrated through the pierce part 23 on the bottom of the container body.

A description will next be made of a using method of the feces sampling container of the present invention having such a constitution. Loosen the gripping part 11 of the feces sampling stick 10, cut and break the label 50 at the perforated line 54 for confirming opening of the container, remove the feces sampling stick 10 from the feces sampling container, and collect feces by sticking the feces sampling part 14 of the feces sampling stick 10 to feces or by smearing it with the surface of the feces. Then, insert the stick part 12 of the feces sampling stick 10 into the erected container body 20 while being guided by the tubular guide part 34a of the upper fitting block 30, and screw the gripping part 11 of the feces sampling stick 10 to engage the male screw part 13 provided at the base end part of the stick part of the feces sampling stick 10 with the female screw part 33 provided at the upper part of the upper fitting block 30 and hermetically seal the container body 20 with the gripping part 11. At this time, the feces sampling part 14 of the feces sampling stick 10 successively passes through the first leveling hole 35 and the second leveling hole 42. Before the feces sampling part 14 of the feces sampling stick 10 reaches the first leveling hole 35, excess feces F attached to the feces sampling part 14 and the like slide down on the downward helix slope 38 of the helical structure 37 due to the adhesive force of the feces while being compressed between the stick and the helical structure 37 protruding to the inner surface side of the tubular guide part 34a. They are accumulated in non-different level portion 39 of the protruding helical structure 37. Since the diameter of the first leveling hole 35 is smaller than the diameter of the stick part 12 of the feces sampling stick 10, the excess feces F are stored in the aforementioned non-different level 39 to give a collected-feces detecting domain.

The feces sampling part 14 of the feces sampling stick 10 passes through the first leveling hole 35, then passes through the tubular guide part 34b while being pressed by the inner wall thereof, and finally reaches the second leveling hole 42, while falling down with a proper amount of feces in a plurality of concave parts 15. Since the material of the lower fitting block 40 provided with the second leveling hole 42 is softer than that of the tubular guide part 34b of the upper fitting block 30 and at the same time, the diameter of the second leveling hole 42 is by far smaller than that of the stick part 12 of the feces sampling stick 10, the feces retained in the plurality of concave parts 15 are leveled to retain a predetermined amount of feces in the feces sampling part 14 of the feces sampling stick 10. The feces sampling part 14 of the feces sampling stick 10 retaining a predetermined amount of feces reaches the liquid for suspending feces 22 enclosed with the lower fitting block 40 and the filter 25, by which screwing of the gripping part 11 of the feces sampling stick 10 is completed. After confirming collection of feces in non-different level portion 39 (collected-feces detecting domain), from the cutout window 53 provided in the label 50 for confirming collection of feces, the subject can send this feces sampling container to hospitals or inspection institutes by mail or another method. The hospital or inspection institute can make a test by reconfirming the collection of feces in the collected-feces detecting domain of the feces sampling container, then penetrating the tip of a suction nozzle of the fecal suspension successively into the label 50 and the pierce part 23 of the concave bottom 21 of the container body while turning the feces sampling container upside down, suctioning the fecal suspension filtered through the filter 25 and sending it to an analysis apparatus.

INDUSTRIAL APPLICABILITY

The present invention provides a feces sampling container useful for colon cancer screening or the like.

EXPLANATION OF LETTERS OR NUMERALS

10 . . . feces sampling stick
11 . . . gripping part of the feces sampling stick
12 . . . stick part of the feces sampling stick
13 . . . male screw part at the base end of the stick part of the feces sampling stick
14 . . . feces sampling part of the feces sampling stick
15 . . . concave part of the feces sampling part
20 . . . container body
21 . . . concave bottom of the container body
22 . . . liquid for suspending feces
23 . . . pierce part
25 . . . filter
26 . . . filter support
30 . . . upper fitting block
31 . . . fitting flange part of the upper fitting block
32 . . . tubular guide member of the upper fitting block
33 . . . female screw part of the tubular guide member
34 . . . tubular guide part of the tubular guide member
35 . . . first leveling hole
36 . . . different level of the tubular guide part
37 . . . helical structure protruding to the inner surface side of the tubular guide part
38 . . . downward helix slope of the helical structure
39 . . . non-different level portion of the helical structure (collected-feces detecting domain)
40 . . . lower fitting block
41 . . . lower fitting block support
42 . . . second leveling hole
43 . . . hold part for the upper fitting block
50 . . . label
51 . . . data entry column
52 . . . barcode
53 . . . cutout window for confirming collection of feces
54 . . . perforated line for confirming opening of the label
55 . . . perforated line for test
F . . . excess feces attached to the feces sampling part

The invention claimed is:

1. A feces sampling container comprising a feces sampling stick, a container body, and a fitting body to be fitted to the inner part of the container body, wherein
the feces sampling stick has a gripping part on one side thereof, a stick part on the other side, and a feces sampling part in the vicinity of the tip of the stick part;
the container body has an opening part for fitting the fitting body therein on one side, a bottom part on the other side, and a feces-suspending liquid container part for preserving a liquid for suspending feces therein in a space between a lower side of the container body and a lower part of the fitting body;
the fitting body has a tubular guide part that enables introduction of the stick part of the feces sampling stick, a first leveling hole provided in the tubular guide part for removing excess feces, wherein the opening area of the first leveling hole of the fitting body is smaller than the cross-sectional area of the feces sampling part of the feces sampling stick, and a second leveling hole provided below the first leveling hole for further removing excess feces, and
a collected-feces detecting domain is formed in the tubular guide part adjacent to an upper end of the first leveling hole.

2. The feces sampling container according to claim 1, wherein the feces sampling stick is equipped, at the base end of the stick part thereof, with a screw part for screwing and inserting the feces sampling stick in the fitting body.

3. The feces sampling container according to claim 1, wherein the feces-suspending liquid container part preserves therein the liquid for suspending feces and the feces sampling part in the vicinity of the tip of the stick part of the feces sampling stick penetrates through the first leveling hole and the second leveling hole of the fitting body and is dipped in the liquid for suspending feces.

4. The feces sampling container according to claim 1, wherein the feces sampling part in the vicinity of the stick part of the feces sampling stick is equipped with a concave part, a through-hole, or a trench part.

5. The feces sampling container according to claim 1, wherein the bottom part of the container body is a recessed bottom equipped with a pierce part.

6. The feces sampling container according to claim 1, wherein an opening area of the second leveling hole of the fitting body is smaller than an opening area of the first leveling hole.

7. The feces sampling container according to claim 2, wherein the collected-feces detecting domain is formed by a helical structure protruding to the inner surface side of the tubular guide part of the fitting body.

8. The feces sampling container according to claim 7, wherein the helical structure is formed so that a helix rotation angle of the feces sampling stick to be screwed and inserted is set at within from 200 to 260 degrees.

9. The feces sampling container according to claim 1, wherein the fitting body is comprised of an upper fitting block and a lower fitting block and the upper fitting block has the first leveling hole of the tubular guide part.

10. The feces sampling container according to claim 9, wherein the lower fitting block has the second leveling hole and a support part for supporting a lower side part of the tubular guide part in the upper fitting block.

11. The feces sampling container according to claim 1, wherein the fitting body further has, below the second leveling hole thereof, a filter part.

12. The feces sampling container according to claim 1, wherein a label is stuck in a J shape to the outside of the feces sampling container, over a part from the gripping part to one of a front side surface, a bottom, and a back side surface of the container body, and the label is provided with a cutout window for confirming a collection of feces, from which the collected-feces detecting domain can be seen directly.

* * * * *